Figures 1, 2:
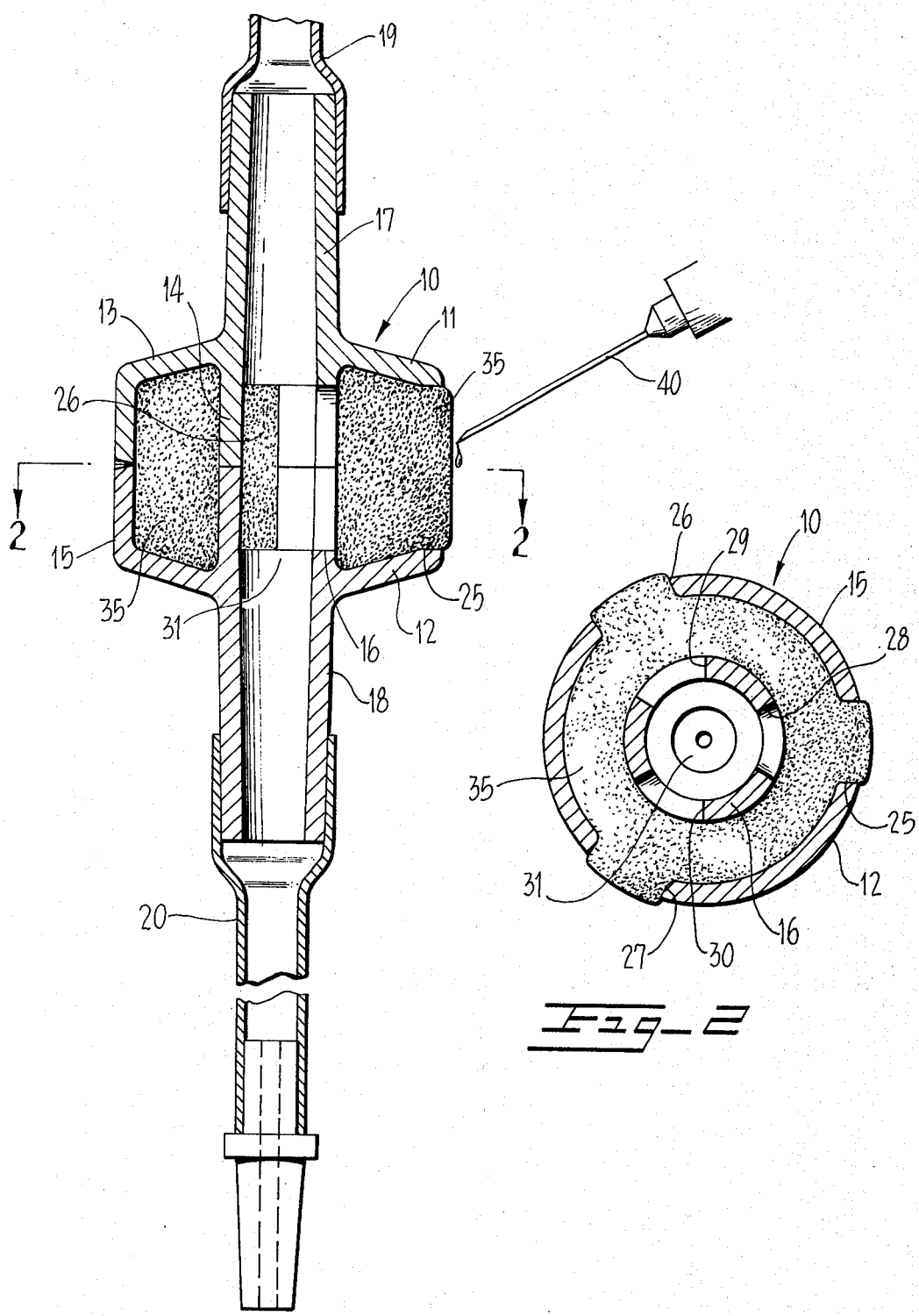

United States Patent [19]
Lundquist

[11] 3,990,445
[45] Nov. 9, 1976

[54] DRUG INJECTION DEVICE
[75] Inventor: Ingemar H. Lundquist, Oakland, Calif.
[73] Assignee: Valleylab, Inc., Boulder, Colo.
[22] Filed: Jan. 3, 1975
[21] Appl. No.: 538,371

[52] U.S. Cl............................ 128/214 R; 138/103
[51] Int. Cl.². ......................................... B61M 5/00
[58] Field of Search ........ 128/214 R, 214 C, 214 Z; 138/103

[56] References Cited
UNITED STATES PATENTS

| | | | |
|---|---|---|---|
| 2,832,338 | 4/1958 | Ryan | 128/214 R |
| 3,447,570 | 6/1969 | Collins | 128/214 R |
| 3,850,202 | 11/1974 | Morgan | 138/103 |
| 3,898,988 | 8/1975 | Morgan | 128/214 R |

*Primary Examiner*—Dalton L. Truluck
*Attorney, Agent, or Firm*—Flehr, Hohbach, Test, Albritton & Herbert

[57] ABSTRACT
A drug injection device (or what some might prefer to call a "drug injection site") comprises a doubled wall, doughnut-shaped cylinder adapted to be inserted into an intravenous delivery tube. Preferably it is made of a pair of identically shaped elements having an outer end an inner circular wall, both of which, when the two elements are placed together in opposed relationship, form continuous walls of a doughnut or O-ring shape. The interior of the doughnut is filled with a soft surgical grade rubber which, when under compression, permits ready insertion of a hypodermic needle therethrough but which, when the needle is withdrawn, is self-sealing. A plurality of radially aligned apertures, or windows, are provided in the inner and outer walls, so that the hypodermic needle can be inserted through the outer wall, through the rubber sealing element and then through the aligned window in the inner wall. Preferably, the windows are three in number, equally spaced around the circumference of the device, so that when a needle is inserted through the respective windows and the rubber sealing element, it will be stopped by an opposing wall of the inner solid surface of the inner wall of the device.

4 Claims, 2 Drawing Figures

DRUG INJECTION DEVICE

BACKGROUND OF THE INVENTION

It is a common practice in hospitals to introduce drugs to a patient through an intravenous feeding line whenever that patient is being fed intravenously. It is obvious that such a practice avoids the pain of repeated injections which accompany direct injection from a hypodermic needle, but it also avoids the danger of infection. Further, the injection into the intravenous feeding liquid causes the drug to be diluted by the liquid and therefore fed more slowly to the patient.

The present invention is directed to providing a site, or location in an intravenous feeding tube through which the drug may be administered and has the advantages that it is kept sterile even at increased liquid pressure, and is selfsealing so that it may be used repeatedly while the patient is being fed intravenously. It is especially designed for use with intravenous feeding pumps, in which case there is an internal build-up which causes leakage problems if conventional sites are used.

OBJECTS

It is an object of the present invention to provide a site, or device, for insertion of a drug into an intravenous feeding tube which can be kept sterile, readily inserted in the delivery tube, is leak-resistant, and which may be used repeatedly.

It is a further object of the present invention to provide a better device for the introduction of a drug to an intravenous feeding solution.

It is a still further object of the present invention to provide a leak-resistant seal for a drug injection site used in a pressurized (pumped) intravenous feeding system.

These and other objects of the invention will be apparent from the specification which follows and taken in connection with the accompanying drawing, in which:

FIG. 1 is a longitudinal, cross-sectional view of the device, on an enlarged scale, such as taken along the transverse plane indicated by the line 1—1 of FIG. 2; and FIG. 2 is a transverse cross-sectional view, such as taken along the longitudinal plane indicated by the line 2—2 of FIG. 1.

The preferred form of the present device 10 comprises a pair of identical sections 11 and 12 preferably formed of a relatively strong and hard medically acceptable plastic 35. Each section 11 and 12 comprises an outer wall 13 and 15, respectively, and an inner wall 14 and 16, respectively, thus forming, when placed in opposing relationship, a doughnut-shaped device. The two sections 11 and 12 are provided with central hollow tubes 17 and 18, respectively, which are adapted to register with a supply tube 19 and a delivery tube 20 for the intravenous feeding liquid. The two sections 11 and 12 are both provided with a plurality of windows (preferably three in number) 25, 26, and 27 in the outer walls 13 and 15 and similar axially aligned windows 28, 29 and 30 in the inner walls 14 and 16, respectively. Thus, a needle inserted radially through the outer window, such as 25, 26 or 27, will also go through the inner windows 28, 29 and 30. It is also obvious from a glance at FIG. 2 that such a needle inserted through any of the three windows will penetrate into the inner bore 31 and will engage a solid inner wall 14 or 16 of the bore. Since the outer and inner walls are formed of a hard and strong plastic, it is difficult to penetrate the walls themselves, so that an operator will immediately know when the needle is in the bore 31 of the device.

The space between the outer and inner walls is filled with a soft surgical grade of rubber 35, somewhat larger than the space to be filled. Since the rubber doughnut is larger than the space to be filled, it must be compressed between the walls and hence will always be under compression when the respective segments 11 and 12 are cemented together to form an integral device. It is also preferred that the annular space formed when the two pieces 11, 12 are placed together, and which holds the doughnut sealing element 35, is thicker at the inner wall than at the outer, so that the internal pressure will force the sealing element even tighter against the outer wall. As shown in the drawing, it is assumed that the rubber seal 35 will bulge somewhat through the outer and maybe even the inner window, but that is immaterial. What is desirable is that the doughnut-shaped rubber sealing element 35 be under slight compression so that there is always a compressive force tending to seal the material after a hypodermic needle is withdrawn.

It is believed that the operation of the device of the present invention is obvious. The device will be supplied as an integral structure for the two respective sections 11 and 12 are cemented together after the doughnut-shaped rubber seal 35 has been inserted into one of them. The entire, or integral, device can then be sterilized, sealed in a sterile container and delivered to the hospital. When needed, the container can be opened, the device 10 inserted between an intravenous feeding supply line 19 and a delivery tube 20 and thence to an intravenous feeding needle, not shown. When a drug is desired to be administered to the patient, a hypodermic needle 40 with the proper dosage is inserted through one of the windows 25, 26 or 27, pushed until resistance is encountered by the needle engaging an opposite inner wall. The drug is then injected through the hypodermic needle 40 and the needle is withdrawn. Since the rubber sealing element is under slight compression and is of a sealing grade soft surgical rubber, the device is self-sealing, both to prevent the seepage of intravenous feeding fluid from the interior of the line to the outer surface, and to prevent the penetration of air from the outside into the interior bore 31.

What is claimed is:

1. A drug injection device for insertion into an intravenous feeding tube comprising: a hollow-doughnut shaped casing having an outer wall and an inner wall and first and second faces, said casing forming a chamber which decreases in thickness from the inner wall to the outer wall, an inlet nipple provided on the first face of the casing and an outlet nipple formed on the second face of the casing, said inlet and outlet nipples being in unobstructed communication one with the other through a conduit formed by the inner wall, self-sealing rubber-like material filling the chamber between the inner and outer walls of said casing and a radially aligned window in the outer and inner walls of said device.

2. In a drug injection device for connection into an intravenous feeding tube, a two-part casing, each of said parts having an inner tubular portion and an outer dish-shaped portion surrounding the inner tubular portion, said inner tubular portion and said outer dish-shaped portion providing an annular space therebetween, means for fastening said two-part casing into a unitary assembly, said outer dish-shaped portions being in contact with each other when said two parts are fastened together a body of self-sealing rubber-like material disposed in said annular recesses in said two parts, said inner tubular portions being in contact and in registration with each other when said two parts are fastened together to provide a flow passage extending through the casing, the outer ends of said inner tubular portions being adapted to be connected into the intravenous feeding tube, said inner tubular portions having at least one opening therein which is covered by the body, said dish-shaped portions having at least one window therein in general alignment with the opening in the tubular portions whereby said window and said opening in combination with the body serve as an injection site.

3. A device as in claim 2 wherein a plurality of circumferentially spaced openings are provided in the tubular portions and which are covered by said body and wherein said dish-shaped portions are provided with a plurality of windows in general alignment with the openings in the tubular portions.

4. A device as in claim 3 wherein said openings in the tubular portions are spaced in such a manner so that wall portions of the tubular portions are immediately opposite each of the openings.

* * * * *